United States Patent [19]

Hässig

[11] Patent Number: 4,918,230
[45] Date of Patent: Apr. 17, 1990

[54] PROCESS FOR THE PREPARATION 4-BROMOANILINE HYDROBROMIDES

[75] Inventor: Robert Hässig, Gipf-Oberfrick, Switzerland

[73] Assignee: Ciba-Geigy Corporation, Ardsley, N.Y.

[21] Appl. No.: 206,551

[22] Filed: Jun. 14, 1988

[51] Int. Cl.[4] .................. C07C 87/452; C07C 85/24
[52] U.S. Cl. ..................... 564/307; 564/412
[58] Field of Search ................. 564/307, 412

[56] References Cited

U.S. PATENT DOCUMENTS

| 1,777,266 | 9/1930 | Kalischer et al. | 564/412 |
|---|---|---|---|
| 2,675,409 | 4/1954 | Orloff et al. | 260/579 |
| 4,328,247 | 5/1982 | Drabek et al. | 424/326 |
| 4,447,647 | 5/1984 | Werner et al. | 564/412 |

FOREIGN PATENT DOCUMENTS

| 0052817 | 6/1982 | European Pat. Off. . |
| 0175649 | 9/1985 | European Pat. Off. . |
| 2098210 | 11/1982 | United Kingdom . |

OTHER PUBLICATIONS

Chem. Ber. (1901), vol. 34, pp. 2242-2263 (see p. 2261).
Chem. Ber. (1900), vol. 33, pp. 1967-1975 (see pp. 1971 & 1974).
Houben-Weyl, Methoden der Org. Chemie, vol. 4, pp. 274-276.
J. Org. Chem., vol. 40 (1975) p. 1867.
Berichte, vol. 56 (1983) p. 2043.

Primary Examiner—Richard L. Raymond
Assistant Examiner—Peter G. O'Sullivan
Attorney, Agent, or Firm—Kevin T. Mansfield

[57] ABSTRACT

4-Bromoaniline hydrobromides of formula I

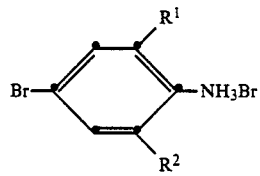

(I)

wherein $R^1$ and $R^2$ are each independently of the other $C_1$–$C_{10}$ alkyl or $C_3$–$C_7$ cycloalkyl, are prepared by brominating an aniline hydrohalide of formula II

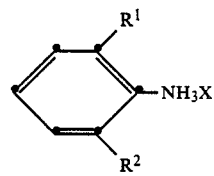

(II)

wherein X is chlorine or bromine and $R^1$ and $R^2$ are as defined above, in the presence of an inert organic solvent.

8 Claims, No Drawings

PROCESS FOR THE PREPARATION 4-BROMOANILINE HYDROBROMIDES

The present invention relates to a process for the preparation of 4-bromoaniline hydrobromides of formula I

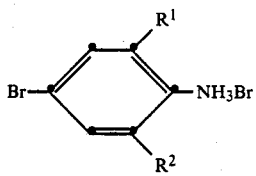
(I)

wherein $R^1$ and $R^2$ are each independently of the other $C_1$–$C_{10}$alkyl or $C_3$–$C_7$cycloalkyl.

The compounds of formula I and the amines from which they are derived are important intermediates for the synthesis of the insecticidally active thiourea and carbodiimide derivatives disclosed, for example, in U.S. patent specification No. 4 328 247 and European patent application 0 175 649.

In the definitions of formula I, alkyl will be understood as meaning straight chain or branched alkyl, for example methyl, ethyl, n-propyl, isopropyl or the four isomers of butyl, n-pentyl or the isomers thereof, hexyl or the isomers thereof, as well as heptyl, octyl, nonyl and decyl, including the isomers thereof. Alkyl radicals of 1 to 4 carbon atoms are preferred, and methyl, ethyl and isopropyl are most preferred.

$R^1$ and $R^2$ as cycloalkyl may suitably be cyclopropyl, cyclobutyl, cyclopentyl, cyclohexyl or cycloheptyl. These radicals can also be substituted by one or more than one alkyl group. Preferred cycloalkyl radicals are cyclopentyl and cyclohexyl. Cyclopentyl is most preferred.

It is known that 4-bromo-2,6-dialkylanilines are predominantly formed by brominating 2,6-dialkylanilines. The high reactivity of these compounds causes the reaction to proceed non-selectively with the formation of different by-products, depending on the reaction conditions. Thus, for example, the bromination of 2,6-dimethylaniline in the presence of glacial acetic acid gives 4-bromo-2,6-dimethylaniline in a yield of 80–85% of theory (Chem. Ber. (1901), 34, 2242). The bromination of 2,6-dimethylaniline in strongly acid medium always results in the formation of substantial amounts of 3-bromo-2,6-dimethylaniline (Chem. Ber. (1900), 33, 1967). It is further known from published UK patent application A 2 098 210 that, in the halogenation of N-alkyl-2,6-dialkylanilines in the presence of a Lewis acid such as AlCl$_3$, the halogen is even introduced selectively in 3-position.

Aside from the unsatisfactory yield, a material drawback of the known processes is that the desired 4-bromo-2,6-dialkylanilines are obtained in insufficient purity, thus necessitating an additional purification of the products by distillation. Such an additional purification is, however, problematical on account of the thermal instability of the bromoanilines. Carrying out the bromination in glacial acetic acid has the additional disadvantage that the working up of the reaction mixture results in the formation of a dilute aqueous solution of sodium acetate from which the acetic acid used as solvent can only be recovered by very laborious means.

It has so far not proved possible to prepare 4-bromo-2,6-dialkylanilines in satisfactory manner by means of the prior art processes. It is therefore the object of the present invention to provide a process that permits 4-bromo-2,6-dialkylanilines to be obtained in simple manner and in good yield and purity.

Surprisingly, it has now been found that 4-bromo-2,6-dialkylaniline hydrobromides of formula I are obtained in almost quantitative yield by brominating 2,6-dialkylaniline hydrohalides of formula II in an inert solvent. The 4-bromodialkylaniline hydrobromides of formula I so obtained can be converted in simple manner into the corresponding 4-bromo-2,6-dialkylanilines.

Accordingly, the present invention relates to a process for the preparation of 4-bromo-2,6-dialkylaniline hydrobromides of formula I, which comprises brominating a 2,6-dialkylaniline hydrohalide of formula II

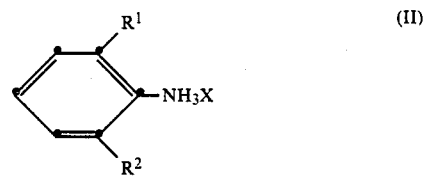
(II)

wherein $R^1$ and $R^2$ are as defined for formula I and X is chlorine or bromine, in the presence of an inert organic solvent.

Starting materials and final products of the process of this invention are known. The aniline hydrohalides of formula II can be obtained from the correspondingly substituted anilines by hydrohalogenation. These anilines are known and can be obtained by known methods. The hydrohalogenation of anilines can be carried out, for example, with hydrogen chloride or hydrogen bromide in the presence of cyclohexane at room temperature.

If desired, the 4-bromoaniline hydrobromides of formula I obtained by the process of this invention can be converted into the corresponding 4-bromoanilines by treatment with aqueous bases by methods conventionally employed in the art.

The process of this invention is conveniently carried out under atmospheric pressure in the temperature range from $-20°$ C. to $+150°$ C., preferably from $-5°$ C. to $+100°$ C., in an inert water-immiscible solvent.

Suitable solvents are open chain or cyclic saturated hydrocarbons and saturated halogenated hydrocarbons. Examples of suitable solvents are: hexane, cyclohexane, methylcyclohexane, dichloromethane, trichloromethane, tetrachloromethane or 1,2-dichloroethane. Preferred solvents are cyclohexane and 1,2-dichloroethane.

The process of this invention is especially suitable for the preparation of 4-bromo-2,6-dialkylaniline hydrobromides of formula I, wherein $R^1$ and $R^2$ are each methyl, ethyl or isopropyl, or $R^1$ is isopropyl and $R^2$ is cyclopropyl.

A preferred variant of the process of this invention comprises preparing the 4-bromoaniline hydrobromides of formula I by brominating an aniline hydrohalide of formula II in the presence of 1,2-dichloroethane or cyclohexane in the temperature range from $-5°$ to $+100°$ C.

The process of this invention makes it possible to prepare 4-bromo-2,6-dialkylanilines in almost quantitative yield. The marked increase in yield compared with the known processes must be regarded as surprising, as the literature shows that the selectivity of the bromination in 4-position is smaller in the case of aniline salts than in that of the free bases [q.v. Houben-Weyl, Methoden der org. Chemie V/4, 236, 274 et seq. (1960)]. An additional advantage of the process of the invention is the use of an inert organic water-immiscible solvent, which enables the free aniline bases to be isolated from the reaction mixture in substantially easier manner than in the processes using acetic acid.

The following Examples illustrate the process of the invention in more detail.

EXAMPLE 1

Preparation of 4-bromo-2,6-diisopropylaniline hydrobromide 19.1 g of bromine are added dropwise at 0° C. over 1 hour to a suspension of 24.1 g of 2,6-diisopropylaniline hydrochloride in 250 ml of 1,2-dichloroethane. The reaction mixture is stirred for 1 hour at 0° C. and then filtered. The filter residue is washed with 1,2-dichloroethane and then dried at 40° C. under vacuum, affording 36.8 g (97% of theory) of 4-bromo-2,6-diisopropylaniline hydrobromide in the form of yellow crystals which melt at 235°–237° C. after recrystallisation from ethyl acetate.

EXAMPLE 2

19.1 g of bromine are added dropwise at 70° C. over 2 hours to a suspension of 24.1 g of 2,6-diisopropylaniline hydrochloride in 150 ml of cyclohexane. The hydrogen chloride evolved in the course of this addition escapes continuously. The reaction mixture is cooled to 10° C. and then filtered. The filter residue is washed with cyclohexane and dried at 40° C. under vacuum, affording 34.1 g of 4-bromo-2,6-diisopropylaniline hydrobromide (99.9% of theory) in the form of yellow crystals of 98.7% purity and having a melting point of 234°–235° C. (compound 1).

The following compounds of formula I are also obtained in accordance with the foregoing procedures:

| Compound | R$^1$ | R$^2$ | Melting point |
|---|---|---|---|
| 2 | CH$_3$ | CH$_3$ | 241–242° C. |
| 3 | C$_2$H$_5$ | C$_2$H$_5$ | 228–231° C. |
| 4 | C$_3$H$_7$(i) | 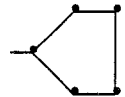 | 256–260° C. |

What is claimed is:
1. A process for the preparation of a 4-bromoaniline hydrobromide of formula I

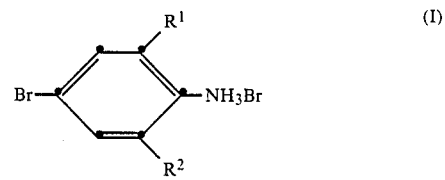

in good yield and purity wherein R$_1$ and R$_2$ are each independently of the other C$_1$–C$_{10}$alkyl or C$_3$–C$_7$cycloalkyl, which process comprises brominating an aniline hydrohalide of formula II

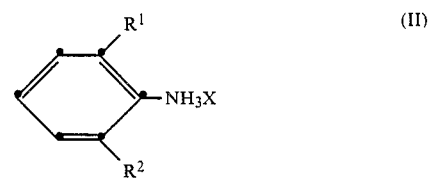

wherein X is chlorine or bromine and R$^1$ and R$^2$ are as defined above, in the temperature range from −20° to +150° C., in the presence of an inert organic solvent.

2. A process according to claim 1, wherein R$^1$ and R$^2$ are each independently of the other C$_1$–C$_4$alkyl or C$_5$–C$_6$cycloalkyl.

3. A process according to claim 1, wherein the solvent is a saturated hydrocarbon or a saturated chlorinated hydrocarbon.

4. A process according to claim 3, wherein the solvent is hexane, cyclohexane, methylcyclohexane, dichloromethane, trichloromethane, tetrachloromethane or 1,2-dichloroethane.

5. A process according to claim 1, wherein each of R$^1$ and R$^2$ is methyl, ethyl or isopropyl, or R$^1$ is isopropyl and R$^2$ is cyclopentyl.

6. A process according to claim 4, wherein the solvent is 1,2-dichloroethane or cyclohexane.

7. A process according to claim 1, which is carried out in the temperature range from −5° to +100° C.

8. A process according to claim 1, which comprises brominating an aniline hydrohalide of formula II in the presence of 1,2-dichloroethane or cyclohexane in the temperature range from −5° to +100° C.

* * * * *